(12) United States Patent
Klassen

(10) Patent No.: US 11,944,719 B2
(45) Date of Patent: Apr. 2, 2024

(54) THIN FILM INTERPOSITION OF BASEMENT MEMBRANE SCAFFOLDS

(71) Applicant: IVIVA Medical, Inc., Beverly, MA (US)

(72) Inventor: Charles C. Klassen, Boston, MA (US)

(73) Assignee: IVIVA Medical, Inc., Woburn, MA (US)

( * ) Notice: Subject to any disclaimer, the term of this patent is extended or adjusted under 35 U.S.C. 154(b) by 579 days.

(21) Appl. No.: 16/470,548

(22) PCT Filed: Dec. 18, 2017

(86) PCT No.: PCT/US2017/067141
§ 371 (c)(1),
(2) Date: Jun. 17, 2019

(87) PCT Pub. No.: WO2018/112480
PCT Pub. Date: Jun. 21, 2018

(65) Prior Publication Data
US 2019/0336647 A1 Nov. 7, 2019

Related U.S. Application Data

(60) Provisional application No. 62/567,748, filed on Oct. 3, 2017, provisional application No. 62/567,746, filed on Oct. 3, 2017, provisional application No. 62/435,121, filed on Dec. 16, 2016.

(51) Int. Cl.
| | |
|---|---|
| A61L 27/36 | (2006.01) |
| A61L 27/18 | (2006.01) |
| A61L 27/38 | (2006.01) |
| A61L 27/40 | (2006.01) |
| A61L 27/52 | (2006.01) |
| A61L 27/54 | (2006.01) |
| A61L 27/56 | (2006.01) |

(52) U.S. Cl.
CPC .......... *A61L 27/3808* (2013.01); *A61L 27/18* (2013.01); *A61L 27/3813* (2013.01); *A61L 27/40* (2013.01); *A61L 27/52* (2013.01); *A61L 27/54* (2013.01); *A61L 27/56* (2013.01)

(58) Field of Classification Search
CPC .. A61L 37/36; A61L 37/3604; A61L 37/3612; A61L 37/362; A61L 37/3625; A61L 37/3629; A61L 37/3633; A61K 9/70
See application file for complete search history.

(56) References Cited

U.S. PATENT DOCUMENTS

| 8,357,528 B2 | 1/2013 | Vacanti et al. |
| 2006/0018838 A1 | 1/2006 | George et al. |
| 2014/0234381 A1 | 8/2014 | Tao et al. |
| 2015/0086607 A1 | 3/2015 | Johnson et al. |

FOREIGN PATENT DOCUMENTS

| JP | 2007-006987 | | 1/2007 | |
| JP | 2007006987 A | * | 1/2007 | |
| WO | WO-03084410 A1 | | 10/2003 | |
| WO | WO 2013/158283 A1 | | 10/2013 | |
| WO | WO-2013158283 A1 | * | 10/2013 | ........... A01N 1/0247 |
| WO | WO 2016/179242 A1 | | 11/2016 | |
| WO | WO 2018/112480 | | 6/2018 | |

OTHER PUBLICATIONS

Robben et al (Significance of thickness of the wall of the renal collecting system in children: an ultrasound study, Pediatric Radiology, 29, 736-740, 1999 (Year: 1999).*
Kolesky et al (3D Bioprinting of Vascularized, Heterogeneous Cell-Laden Tissue Constructs, Advanced Materials, 26, 3124-3130, 2014) (Year: 2014).*
Li Yuanyuan et al (Topographic characterization and protein quantification of esophageal basement membrane for scaffold design reference in tissue engineering; J Biomed Mater Res Part B, 2012: 100B:265-273) (Year: 2012).*
Beardslee et al (Sacrificial Process for Fabrication of Polymer Membranes with Sub-Micron Thickness, J Biomed Mater Res Part B 2016:104B:1192-1201 ). (Year: 2016).*
Kim et al (Recellularization of decellularized human adipose-tissue-derived extracellular matrix sheets with other human cell types; Cell Tissue Res (2012) 348:559-567 (Year: 2012).*
Beardslee et al (Sacrificial Process for Fabrication of Polymer Membranes with Sub-Micron Thickness, J Biomed Mater Res Part B 2016:104B:1192-12011 ) (Year: 2016).*
Bruggeman, L. A., et al. "A cell culture system for the structure and hydrogel properties of basement membranes; Application to capillary walls. Cellular and molecular bioengineering. 2012; 5 (2): 194-204."
Kolesky, David B., et al. "3D bioprinting of vascularized, heterogeneous cell-laden tissue constructs." *Advanced materials* 26.19 (2014): 3124-3130.
Wikipedia, "PLGA" (Aug. 31, 2016) [online] [retrieved on Feb. 16, 2018]. Retrieved from the internet <URL: https://en.wikipedia.org/w/index.php?title+PLGA&oldid=737066597> p. 1.
Jeffrey H. Miner Ed—Ruas Jorge, et al., "The Glomerular Basement Membrane," Experimental Cell Research, vol. 317, No. 9, (2012), pp. 973-978.
Ranjay Jayadev et al: "Current Biology Basement membranes", Current Biology, (2017), pp. 199-217.
Drzezo: "Histologic Features | Abdominal Key", (2016), URL:https://abdomalkey.com/histologic-features/.
International Search Report issued in International Application No. PCT/US2017/067141, dated Mar. 12, 2018.
Extended European Search Report issued in Application No. EP 17 88 2010, dated Jul. 8, 2020.

* cited by examiner

*Primary Examiner* — Micah Paul Young
(74) *Attorney, Agent, or Firm* — Morse, Barnes-Brown & Pendleton, P.C.; Lisa M. Warren, Esq.

(57) ABSTRACT

Disclosed are compositions and methods of making basement membrane constructs having interior or luminal volumes. The interior or luminal volumes may be in the form of vascular networks for liquid (e.g., blood) or gas perfusion. The interior spaces may also contain cells, such as epithelial cells. Also disclosed are tissues and organs, and methods of making thereof, comprising basement membrane constructs.

19 Claims, 8 Drawing Sheets

THIN FILM INTERPOSITION OF BASEMENT MEMBRANE SCAFFOLDS

CROSS-REFERENCE TO RELATED APPLICATIONS

This application is a national stage filing under 35 U.S.C. 371 of International Application No. PCT/US2017/067141, filed Dec. 18, 2017, which claims the benefit of U.S. Provisional Application No. 62/435,121, filed on Dec. 16, 2016, U.S. Provisional Application No. 62/567,746, filed on Oct. 3, 2017, and U.S. Provisional Application No. 62/567,748, filed on Oct. 3, 2017, the contents of which are hereby incorporated by reference in their entireties. International Application No. PCT/2017/067141 was published under PCT Article 21(2) in English.

BACKGROUND OF THE INVENTION

Bioengineering of tissues and organ grafts of human scale requires the generation of a matrix that provides the three-dimensional context for cells to reside and fulfill their function, and supplies a perfusable vascular system to meet the respective tissue metabolic demands. Such matrixes or scaffolds have been generated using techniques including lithography, stereolithography, electrospinning, photopolymerization, and extrusion printing among other techniques. To date, the creation of a vascular channel network has been a major limiting factor in this process. Most recently, techniques such as multidirectional 3D printing using fugitive ink have enabled the generation of three-dimensional channel networks within a solid block of material. This technique can be applied to generate solid tissues such as skeletal muscle, or cartilage.

In contrast to these examples, tissues and organs that contain one or more epithelial structures (digestive, endocrine, nervous, lymphatic, integumentary, reproductive, respiratory, sensory, urinary, and circulatory) depend on the presence of a thin basement membrane that enables functions such as filtration of fluid (kidney, eye, lymphatic, brain), diffusion of gases (lung), secretion and absorption of electrolytes and other molecules (kidney, gut, liver, enteric tissue), and diffusion of hormones (pancreas, pituitary gland, adrenal gland) from one lumen or compartment to another. In many instances, this basement membrane has to be <1 µm or <10 µm thick to enable function (kidney, lung).

Currently, the inventors are not aware of any technology that exists to generate a scaffold containing one or multiple three-dimensional channel networks lined by such a basement membrane. Three-dimensional additive printing technology has significant limitations presented by resolution and material constraints which have to this point prohibited development of tissue constructs containing physiologically accurate vascular structures.

SUMMARY OF THE INVENTION

In some embodiments, the present invention addresses the need for a scaffold containing one or multiple three-dimensional channel networks lined by a basement membrane, and provides novel methods for generating a three-dimensional channel network lined by a basement membrane of defined thickness and composition. This vascular construct can be embedded in support material with or without cells, and can be repopulated with epithelial cell lining to enable higher-level function.

Some embodiments of the invention are directed to a composition (e.g., basement membrane construct, vascularized basement membrane construct, tissue, organ) comprising one or more thin films (also sometimes referred herein as a membrane, thin film membrane, or thin film membrane component) defining an interior volume (e.g., a luminal compartment), wherein the one or more thin films comprise functional basement membrane material. In some embodiments, the interior volume has a top side and a bottom side, and a thin film defines the top side and a polymer or hydrogel defines the bottom side (e.g., the interior volume is sandwiched between the thin film and the basement membrane). In some embodiments, a thin film defines both the top side and the bottom side (e.g., the interior volume is sandwiched between one or two thin films).

In some embodiments, at least one thin film is capable of fluid filtration, gas diffusion, secretion or absorption of an electrolyte, and/or diffusion of a hormone across the thin film. For example, a thin film may be suitable for performing hemodialysis, blood gas exchange for respiration; the absorption of nutrients into the blood for digestion, or introduction of a hormone into the blood for endocrine functions.

In some embodiments, the one or more thin films has a thickness of about 0.1 µm to about 100 µm, of about 0.1 µm to about 100 µm, of about 0.5 µm to about 50 µm, of about 1.0 µm to about 40 µm, of about 5.0 µm to about 30 µm, or of about 10 µm to about 20 µm, or any range therebetween. In some embodiments, the one or more thin films has a thickness of about 10 µm or less. In some embodiments, the one or more thin films has a thickness of about 1 µm or less.

In some embodiments, the interior volume comprises one or more channels (e.g., at least 1, 2, 3, 4, 5, 6, 7, 8, 9, 10, 11, 12, 13, 14, 15, 16, 17, 18, 19, 20, 25, 30, 40, 50, 100, 200, 500, 750, 1000, 2000, 10000 channels). In some embodiments, the at least one channel comprises a branching channel network having one or more branches with decreasing diameters (e.g., at least 1, 2, 3, 4, 5, 6, 7, 8, 9, 10, 11, 12, 13, 14, 15, 16, 17, 18, 19, 20, 25, 30, 40, 50, 100, 200, 500, 750, 1000, 2000, 10000 branches). In some embodiments, channel diameters can include, but not be limited to, about 10 cm, 10 mm, 5 mm, 1 mm, 500 µm, 50 µm, 10 µm, 5 µm, 3 µm, 1 µm, 0.5 µm, 0.1 µm, 0.05 µm, 0.02 µm, or 0.01 µm.

In some embodiments, the interior volume is connected to an exterior space. For example, the interior volume may have a channel that can be operably connected to an artery of a patient and a channel connected to a vein of a patient, enabling blood flow through the interior volume (e.g., through an interior volume forming a vascular network).

In some embodiments, the interior volume forms a vascular channel network. For example, the interior volume can mimic the structure of vascular networks in the lungs, kidney, digestive tract or other tissues of the human body. In some embodiments, the vascular channel network has a volume of about 0.01 mL to about 10 L, of about 0.1 mL to about 5 L, of about 1 mL to about 1 L, of about 10 mL to about 0.5 L, of about 50 mL to about 250 mL, or of about 75 mL to about 150 mL, or any ranges therebetween.

In some embodiments, the functional basement membrane material comprises decellularized tissue. In some embodiments, the decellularized tissue has been liquefied or homogenized. In some embodiments, the functional basement membrane material comprises collagen, gelatin, hydrogel, polylactic acid, chitosan, and/or other biocompatible materials or composites of these materials.

In some embodiments, the thin film is cured, crosslinked, polymerized, dried, and/or gelated.

In some embodiments, the composition comprises multiple films defining multiple interior volumes in a three-dimensional space. For example, the composition can comprise a first interior volume that is a vascular network for blood and a second interior volume separated from the first interior volume by a thin film In some embodiments, the composition further comprises a cellular scaffold. In some embodiments, the cellular scaffold is derived from a decellularized tissue or organ.

In some embodiments, the composition further comprises one or more cell types in the interior volume and adhered to the surface of one or more thin films. In some embodiments, the one or more cell types include an epithelial cell type. "Epithelial cell" refers to a cell or cells that line hollow organs, as well as those that make up glands and the outer surface of the body. In general, there can be considered four types of epithelial cells: squamous epithelial cells, columnar epithelial cells, adenomatous epithelial cells and transitional epithelial cells. In some embodiments, the epithelial cell type is selected from prostate cells, mammary cells, hepatocytes, pancreatic islet cells including beta cells, pulmonary epithelial cells, kidney cells, bladder cells, stomach epithelial cells, large and small intestinal epithelial cells, urethral epithelial cells, testicular epithelial cells, ovarian epithelial cells, cervical epithelial cells, thyroid cells, parathyroid cells, adrenal cells, thymus cells, gall bladder cells, and pituitary cells.

In some embodiments, the composition further comprises one or more cell types in the interior volume and adhered to the surface of one or more thin films. In some embodiments, the one or more cell types include a stem cell or progenitor cell type. "Stem cell" refers to a cell or cells that are not terminally differentiated and may produce, mature, or otherwise transform into cells of a different type. Stem cells may include totipotent, pluripotent, multipotent, oligipotent and unipotent stem cells. Specific examples of stem cells include embryonic stem cells, fetal stem cells, adult stem cells, and induced pluripotent stem cells (iPSCs) (e.g., see U.S. Published Application Nos. 2010/0144031, 2011/0076678, 2011/0088107, 2012/0028821 all of which are incorporated herein by reference).

In some embodiments, the composition comprises a first interior volume that is a first vascular network comprising human vascular endothelial cells and a second interior volume that is a second vascular network comprising human renal epithelial cells, wherein the composition, when connected to a blood circulation system of a patient, is capable of hemodialysis. For example, the composition can be used to supplement or replace kidney tissue of a patient. In some embodiments, the composition is implanted in the patient. In some embodiments, the composition is extracorporeal to the patient.

In some embodiments, the composition comprises a first interior volume that is a first vascular network comprising human vascular endothelial cells and a second interior volume that is a second vascular network comprising human pulmonary epithelial cells, wherein the composition, when connected to a blood circulation system of a patient, is capable of gas exchange. For example, the composition can be used to supplement or replace lung tissue of a patient. In some embodiments, the composition comprises elastic fibers which enable expansion and contraction of the composition. In some embodiments, the composition is implanted in the patient. In some embodiments, the composition is extracorporeal to the patient.

In some embodiments, the composition comprises a first interior volume that is a first vascular network comprising human vascular endothelial cells and a second interior volume that is one or more luminal spaces comprising human intestinal epithelial cells, and interstitial cells and muscle cells outside of the interior volumes, wherein the composition is capable of peristalsis and, when connected to a blood circulation system of a patient, is capable of nutrient absorption into the blood of the patient. For example, the composition can be used to supplement or replace a portion of a digestive tract of a patient.

In some embodiments, the composition comprises a first interior volume that is a first vascular network comprising human vascular endothelial cells and a second interior volume that is a second vascular network comprising human endocrine cells, wherein the composition, when connected to a blood circulation system of a patient, is capable of diffusing hormones or other substances into the blood of the patient. For example, the composition can be used to supplement or replace thyroid, parathyroid, adrenal, thymus, and/or pituitary tissue of a patient.

In some embodiments, the composition is a tissue or organ construct.

Some aspects of the invention are directed to a method of making a basement membrane construct, comprising generating a sacrificial structure (sometimes referred to herein as channel compartment or channel network components) comprising one or more sacrificial materials on a support structure or a thin film layer; applying a thin film layer comprising functional basement membrane material to the sacrificial structure; optionally repeating steps (a) and then (b) one or more times; optionally embedding the product of steps (a), (b) and optionally (c) in a sacrificial or permanent material; and removing the sacrificial material to provide one or more interior volumes, thereby making a basement membrane construct.

In some embodiment, the sacrificial material has a thermally reversible gelation property or can undergo a phase change after application of heat or cold. Any suitable material can be a sacrificial material if it can be removed without removal, degradation, and/or damage to the thin film and/or permanent material. In some embodiments, the sacrificial material is soluble under conditions wherein the thin film and/or permanent material are not soluble. In some embodiments, the sacrificial material is chemically or enzymatically digestible under conditions wherein the thin film and/or permanent material are not digestible. In some embodiments the sacrificial material is a polymer or hydrogel.

In some embodiment, the sacrificial structure of step (a) is generated by extrusion, molding, milling, or additive printing. The method of generating the sacrificial structure is not limited and may employ any suitable method in the art.

In some embodiments, the sacrificial material defines an interior space (e.g., luminal space) as described herein. In some embodiments, the sacrificial structure has a volume defining at least one channel (e.g., at least 1, 2, 3, 4, 5, 6, 7, 8, 9, 10, 11, 12, 13, 14, 15, 16, 17, 18, 19, 20, 25, 30, 40, 50, 100, 200, 500, 750, 1000, 2000, 10000 channels). In some embodiments, the at least one channel comprises a branching channel network having branches with decreasing diameters (e.g., at least 1, 2, 3, 4, 5, 6, 7, 8, 9, 10, 11, 12, 13, 14, 15, 16, 17, 18, 19, 20, 25, 30, 40, 50, 100, 200, 500, 750, 1000, 2000, 10000 branches). In some embodiments, channel diameters can include, but not be limited to, about 10 cm, 10 mm, 5 mm, 1 mm, 500 μm, 50 μm, 10 μm, 5 μm, 3 μm, 1 μm, 0.5 μm, 0.1 μm, 0.05 μm, 0.02 μm, or 0.01 μm.

In some embodiments, the sacrificial structure has a volume defining a vascular channel network or luminal spaces. In some embodiments, the vascular channel network or luminal spaces define a volume of about 0.01 mL to about 10 L, of about 0.1 mL to about 5 L, of about 1 mL to about 1 L, of about 10 mL to about 0.5 L, of about 50 mL to about 250 mL, or of about 75 mL to about 150 mL, or any ranges therebetween.

In some embodiments, the channel network or luminal space is defined through stamping, molding, or other techniques known in the art that will produce a negative space within the scaffold material or a portion of the scaffold material. This space is then encompassed or sealed by addition of the thin film membrane (FIG. 6).

In some embodiments, the channel network or luminal space is defined through selective bonding of thin film membrane(s). For example in some embodiments two thin film membrane pieces may be overlaid and selectively melted, glued, crosslinked, or otherwise bonded to each other in a pattern such that an interior space or channel network is formed between the two membranes (FIG. 7).

In some embodiments, the support structure comprises a cellular scaffold. In some embodiments, the cellular scaffold is derived from a decellularized tissue or organ.

In some embodiments, the thin film of step (b) is applied by chemical or physical thin film deposition, atomization, spraying, electrospinning, or gelation. Any suitable method of thin film deposition may be used and is not limited.

In some embodiments, the thin film of step (b) has a thickness of about 0.1 μm to about 100 μm, of about 0.1 μm to about 100 μm, of about 0.5 μm to about 50 μm, of about 1.0 μm to about 40 μm, of about 5.0 μm to about 30 μm, or of about 10 μm to about 20 μm, or any range therebetween. In some embodiments, the thin film of step (b) has a thickness of about 10 μm or less. In some embodiments, the thin film of step (b) has a thickness of about 1 μm or less.

In some embodiments, the thin film is cured, partially or fully crosslinked, polymerized, dried, or gelated after performance of step (b). Any suitable method of curing, crosslinking, polymerizing, drying, or gelating may be used and is not limited.

In some embodiments, the functional basement membrane material comprises decellularized tissue, organ, or extra-cellular matrix that has been liquefied or homogenized. In some embodiments, the functional basement membrane material comprises collagen, nitrocellulose, gelatin, hydrogel, or polylactic acid.

In some embodiments, the basement membrane construct of step (e) comprises one or more interior volumes between each thin film layer. For instance, the basement membrane construct may comprise, e.g., three thin film layers and two interior volumes, with one of the thin film layers contacting both interior volumes. In some embodiments, the basement membrane construct of step (e) comprises one or more interior volumes between alternating thin film layers. For example, the basement membrane construct may comprise, e.g., four thin film layers and two interior volumes, with each thin film layer contacting only one interior volume. In some embodiments, the basement construct comprises portions having one or more interior volumes between each thin film layer and portions having one or more interior volumes between alternating thin film layers. In some embodiments, the basement membrane construct comprises one thin film membrane and a support structure with one or more interior volumes or luminal spaces between the thin film membrane and support structure. In some embodiments, the basement membrane construct comprises two thin film membranes and one or more interior volumes or luminal spaces between the thin film membranes.

In some embodiments, step (e) further comprises subjecting the sacrificial material to a phase change or de-gelation by application of heat prior to removal of the sacrificial material.

In some embodiments, the method further comprises a step (f) of populating the one or more interior volumes with one or more cell types. In some embodiments, the one or more cell types comprise an epithelial cell type. In some embodiments, the epithelial cell type is selected from prostate cells, mammary cells, hepatocytes, pancreatic islet cells including beta cells, pulmonary epithelial cells, kidney cells, bladder cells, stomach epithelial cells, large and small intestinal epithelial cells, urethral epithelial cells, testicular epithelial cells, ovarian epithelial cells, cervical epithelial cells, thyroid cells, parathyroid cells, adrenal cells, thymus cells, gall bladder cells, and pituitary cells.

In some embodiments, the method further comprises a step (g) of populating the construct with cells exterior to the one or more interior volumes.

In some embodiments, the basement membrane construct of step (e) comprises a first interior volume that is a first vascular network comprising human vascular endothelial cells and a second interior volume that is a second vascular network comprising human renal epithelial cells, wherein the composition, when connected to a blood circulation system of a patient, is capable of hemodialysis. For example, the composition can be used to supplement or replace kidney tissue of a patient.

In some embodiments, the basement membrane construct of step (e) comprises a first interior volume that is a first vascular network comprising human vascular endothelial cells and a second interior volume that is a second vascular network comprising human pulmonary epithelial cells, wherein the composition, when connected to a blood circulation system of a patient, is capable of gas exchange. For example, the composition can be used to supplement or replace lung tissue of a patient.

In some embodiments, the basement membrane construct of step (e) comprises a first interior volume that is a first vascular network comprising human vascular endothelial cells and a second interior volume that is one or more luminal spaces comprising human intestinal epithelial cells, and interstitial cells and muscle cells outside of the interior volumes, wherein the composition is capable of peristalsis and, when connected to a blood circulation system of a patient, is capable of nutrient absorption into the blood of the patient. For example, the composition can be used to supplement or replace a portion of a digestive tract of a patient.

In some embodiments, the basement membrane construct of step (e) comprises a first interior volume that is a first vascular network comprising human vascular endothelial cells and a second interior volume that is a second vascular network comprising human endocrine cells, wherein the composition, when connected to a blood circulation system of a patient, is capable of diffusing hormones or other substances into the blood of the patient. For example, the composition can be used to supplement or replace thyroid, parathyroid, adrenal, thymus, and/or pituitary tissue of a patient.

The above discussed, and many other features and attendant advantages of the present inventions will become better understood by reference to the following detailed description of the invention.

DETAILED DESCRIPTION OF THE INVENTION

Figures 1A, 1B, 1C:
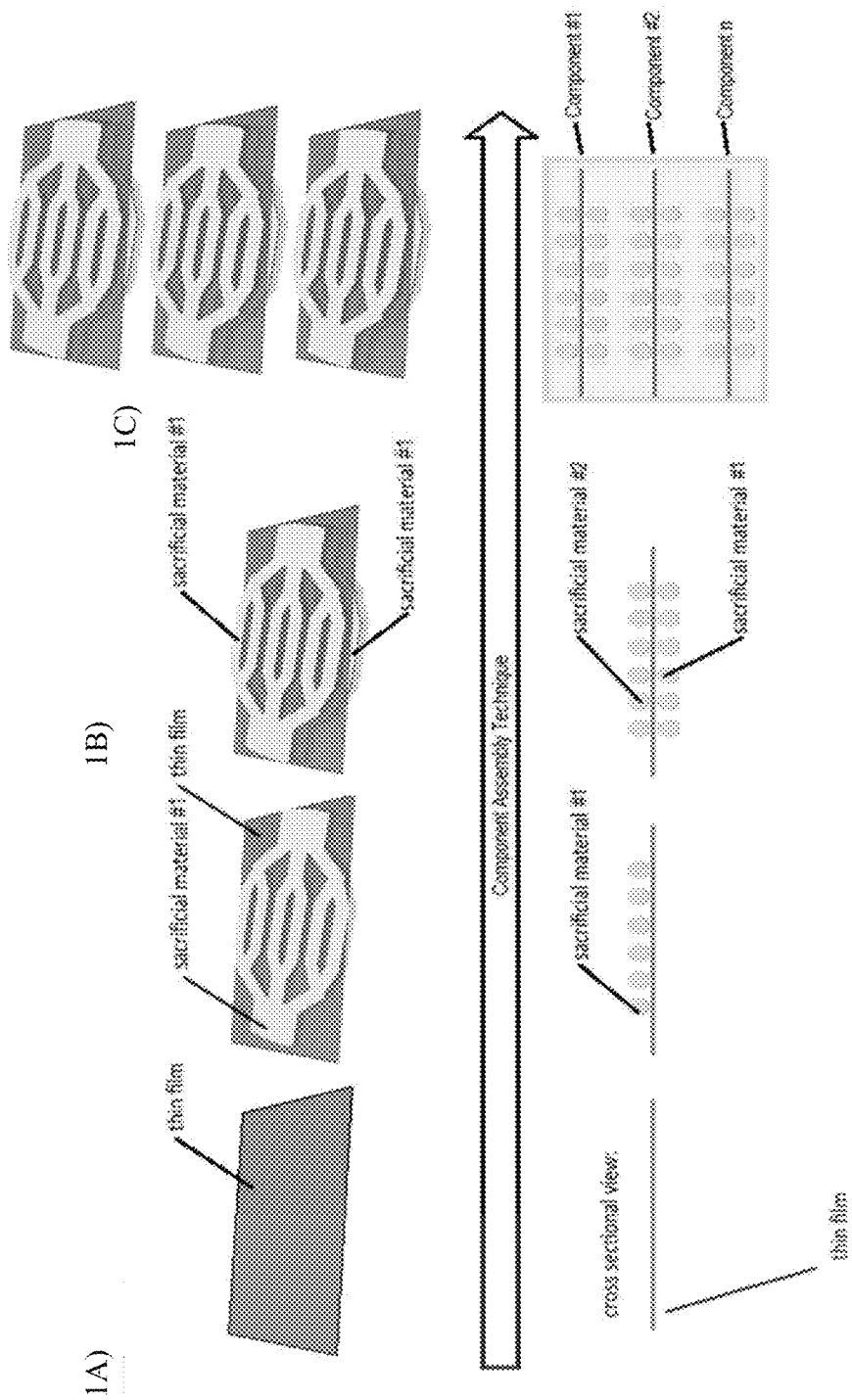
FIGS. 1A-1C depict a component based method of thin film membrane scaffold assembly in which the membrane is created as a stand-alone component which is then incorporated into the scaffold: A) a thin film membrane is created, B) sacrificial material is deposited on the membrane to form channel network(s) on one or more sides, and C) the membrane and channel component(s) may be embedded in a scaffold material to form the scaffold construct.
Figures 2A, 2B, 2C:
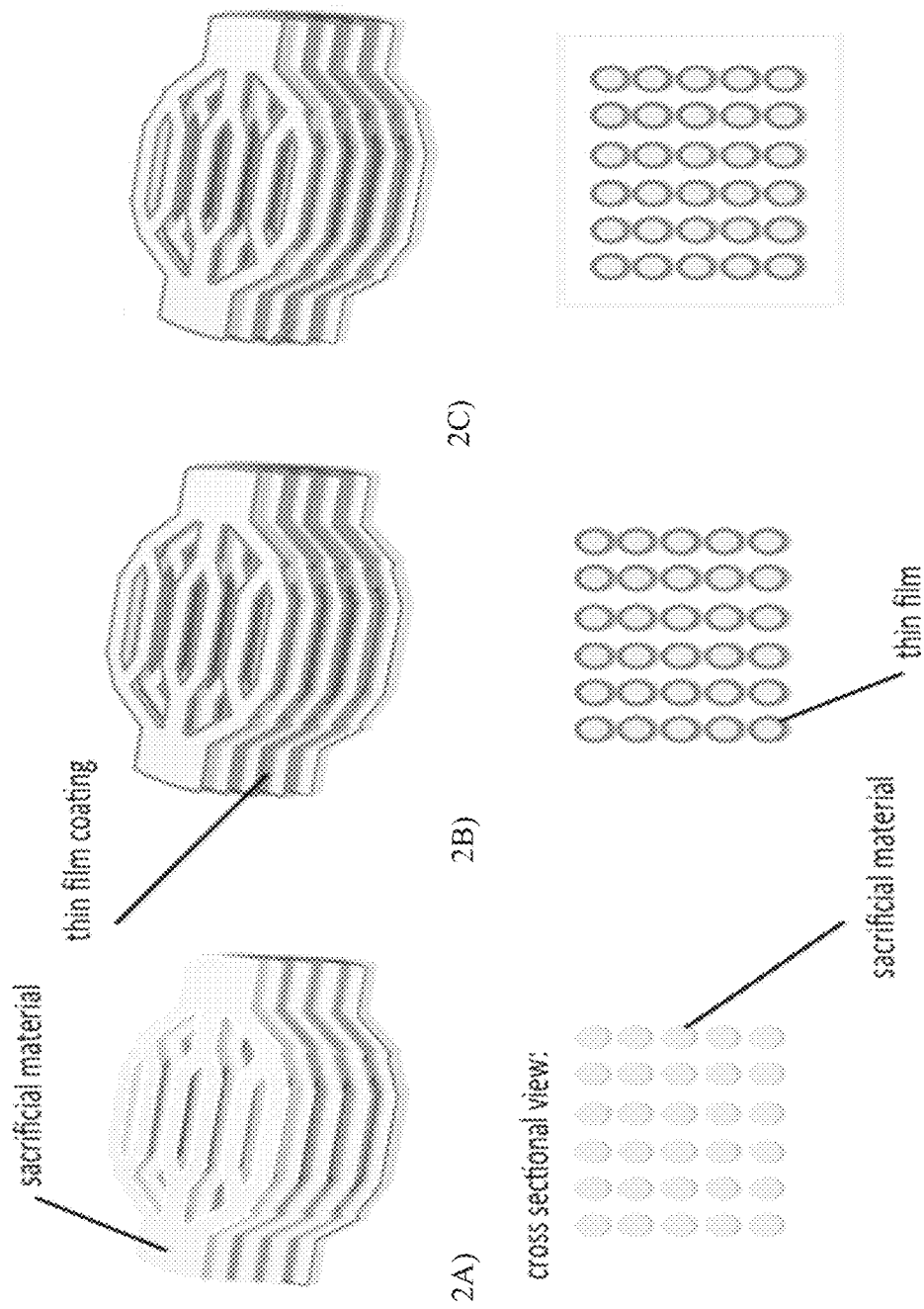
FIGS. 2A-2C depict a sequential method of thin film membrane scaffold assembly in which the membrane is deposited or otherwise created onto or in conjunction with channel network(s) or other scaffold components: A) sacrificial material is deposited to form channel networks, B) a thin film membrane is deposited or otherwise created in conjunction with the channel networks, and C) the membrane and channel component(s) are embedded in a scaffold material to form the construct.
Figures 3A, 3B, 3C, 3D:
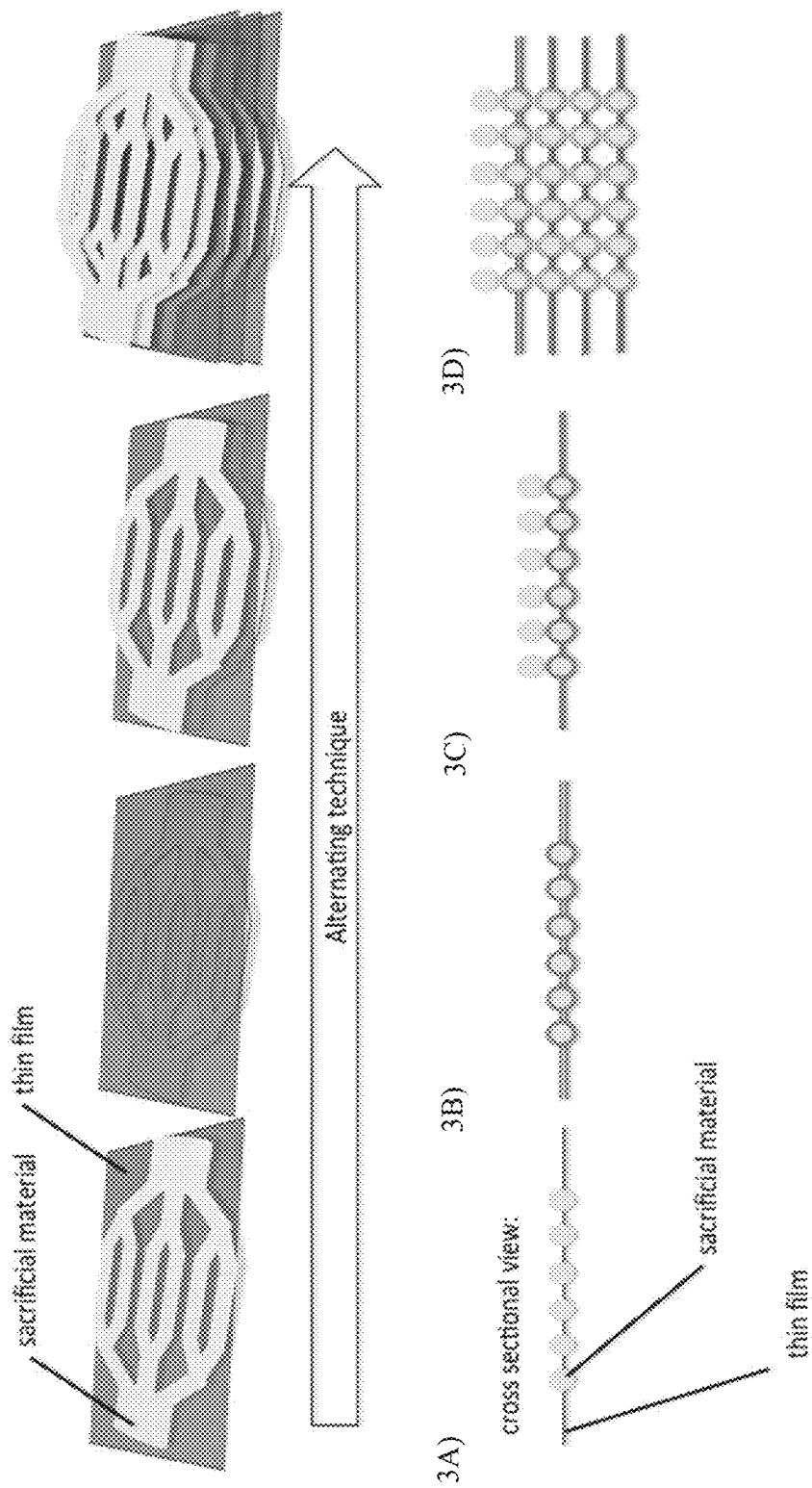
FIGS. 3A-3D depict an alternating method of thin film membrane scaffold assembly in which the membrane is deposited or otherwise created onto or in conjunction with channel network(s) or other scaffold components, and this process is repeated to form larger and or more complex scaffolds: A) a thin film membrane and sacrificial material are deposited to form initial channel network(s), B) a second thin film membrane layer is deposited, C) an additional sacrificial material layer is deposited, and D) the process is repeated to form larger scaffolds.
Figures 4A, 4B, 4C:
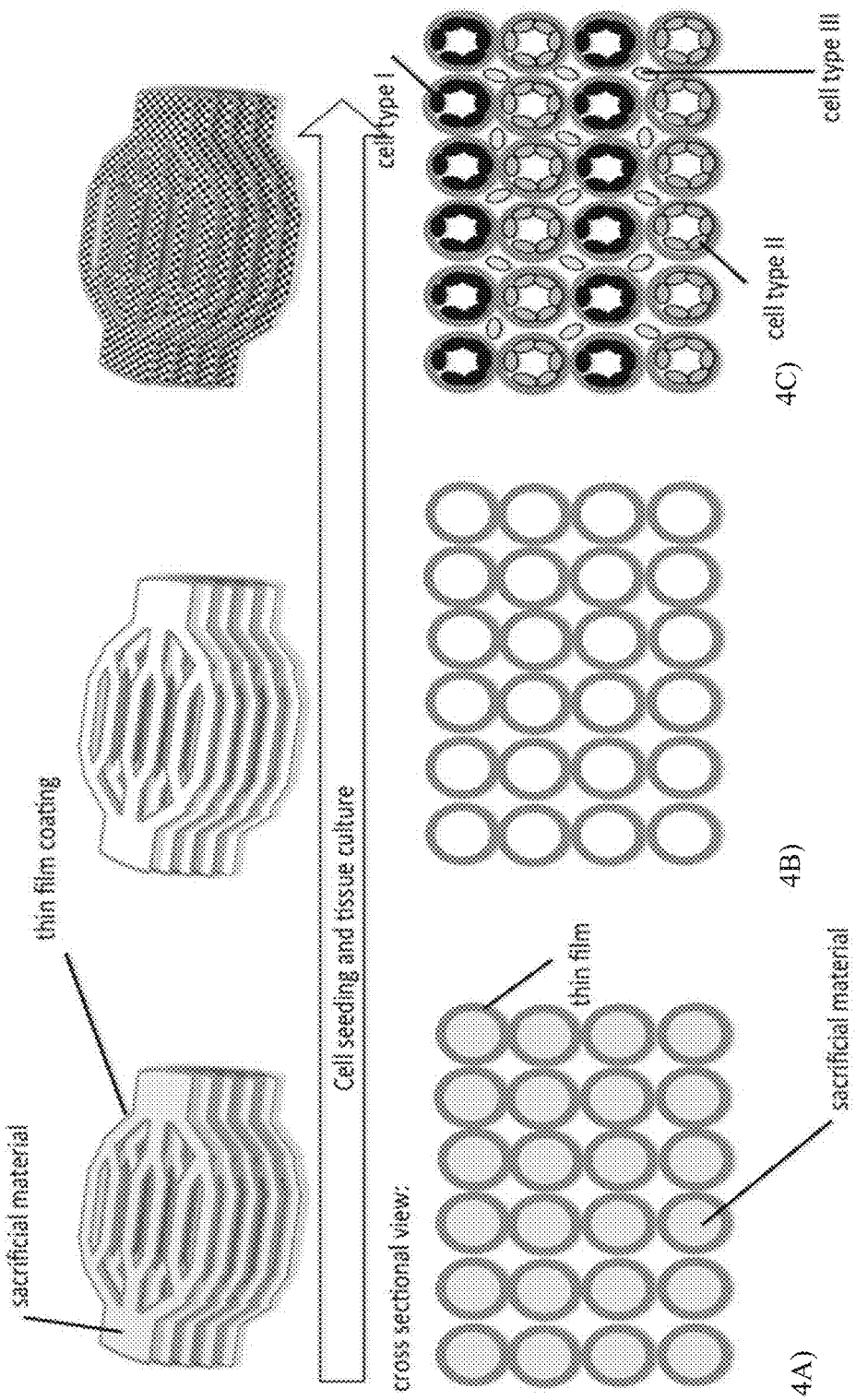
FIGS. 4A-4C depict a method of cellular seeding for the completed scaffold construct: A) the acellular scaffold is created, B) the fugitive material is removed forming the negative space for the channel network(s), and C) multiple cell populations are seeded into the scaffold and channel networks.
Figures 5A, 5B, 5C:
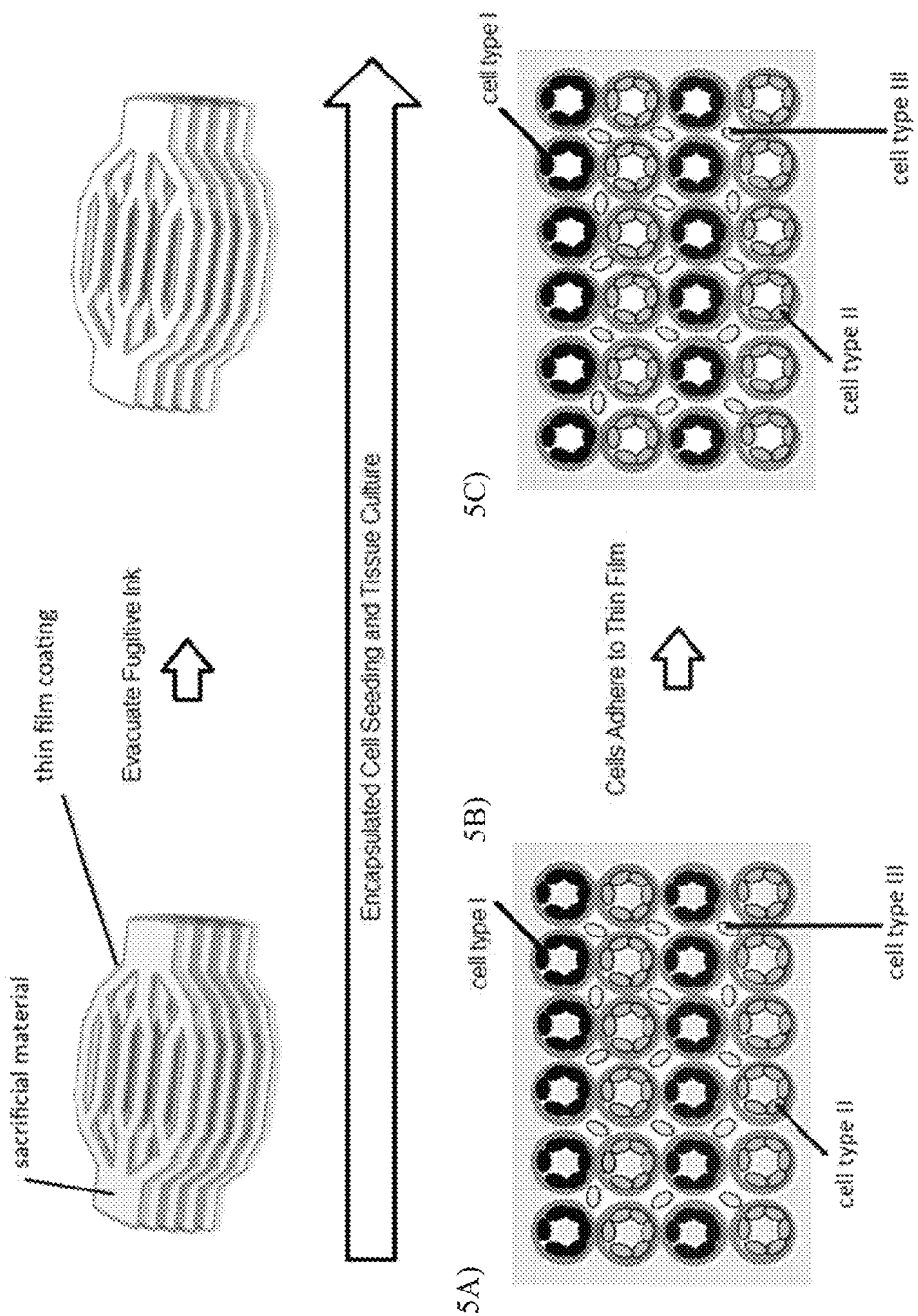
FIGS. 5A-5C depict an alternate method for cellularization of the scaffold construct: A) the cells are embedded, encapsulated, or otherwise contained in the materials used to construct the scaffold, B) as the scaffold is crosslinked, cultured, or otherwise stabilized, the cells adhere to the scaffold, and C) the fugitive material is removed from the channel networks leaving the cell content lining the negative space.
Figures 6A, 6B, 6C:
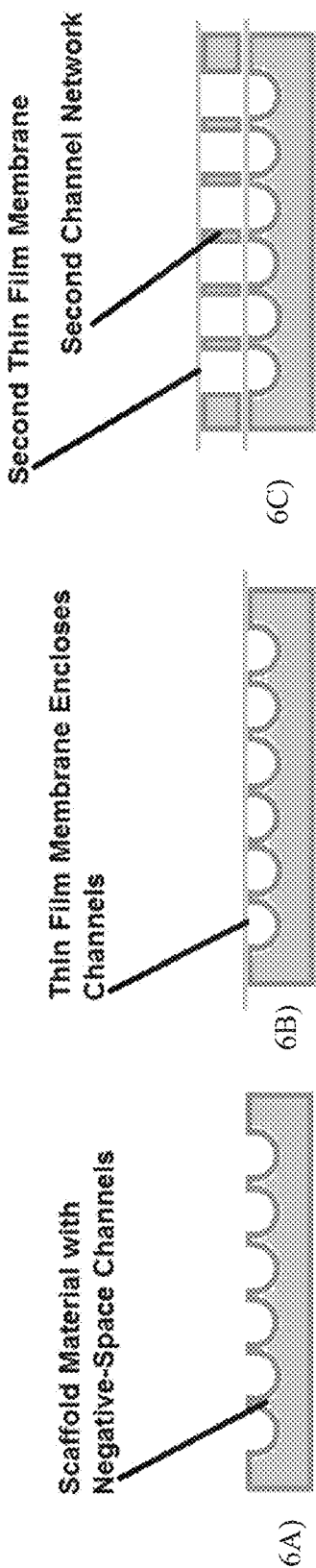
FIGS. 6A-6C depicts an alternate method for construct of the channel network or luminal space, defined through stamping, molding, or other techniques known in the art that will produce a negative space within the scaffold material or a portion of the scaffold material: A) the scaffold material is molded to create negatives of the channel network(s) or luminal spaces, B) the thin film membrane is crosslinked or otherwise bonded to the scaffold material creating enclosed channel networks, and C) a second scaffold material component is molded and added to the construct to create a second channel network. This process may be repeated sequentially.
Figures 7A, 7B, 7C:
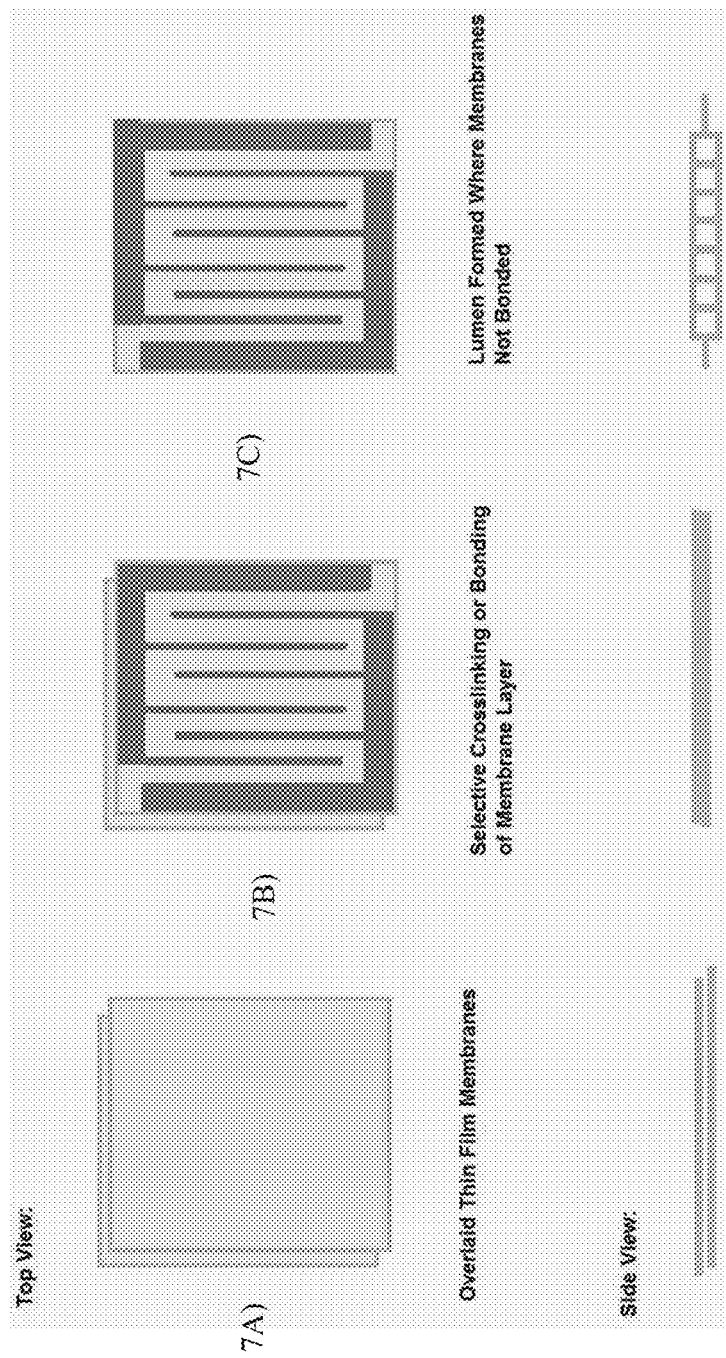
FIGS. 7A-7C depicts an alternate method for construct of the channel network or luminal space, which is defined through selective bonding of thin film membrane(s): A) Two thin film membrane pieces may be overlaid, B) the membranes are selectively melted, glued, crosslinked, or otherwise bonded to each other in a pattern such that an interior space or channel network is formed between the two membranes, C) luminal space formed in regions not having bonded membranes.
Figure 8:
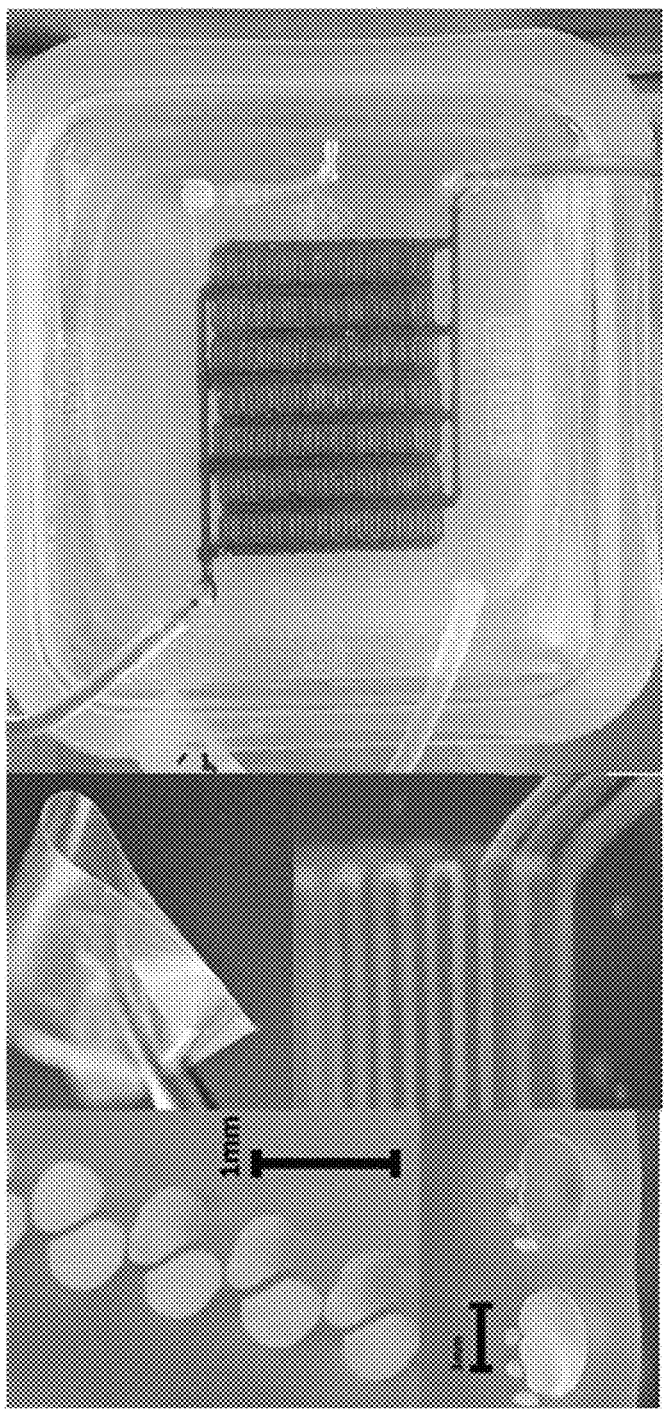
FIG. 8 depicts examples of thin film membranes, scaffolds, channel networks, and organ specific architecture created using these techniques described herein for construction of thin film membrane scaffolds.

In some embodiments, the invention disclosed herein addresses a critical component needed for engineering functional organ tissue constructs by creating a biomimetic membrane within organ scaffolds that can perform the same function as basement membrane in native organ tissue, i.e. filtration, diffusion, absorption, and secretion. In some embodiments, the invention covers methods of constructing biological thin film membranes of varying composition and properties that may be incorporated into scaffolds for tissue engineering. These scaffolds may be of varying material composition and contain one or more channel network(s) of varying architecture capable of containing or transporting fluid, gas, or other materials. These channel(s) are adjacent to or lined with the thin film membrane(s) of varying composition. A general concept of some embodiments of the invention is depicted in FIG. 1. Specifically, in this embodiment the thin film membrane partially or fully encompasses a compartment, channel, or channel network and another adjacent compartment, channel, or channel network, defining the boundary between these two compartments, channels, or channel networks. This membrane and channel architecture comprises the functional portion of the scaffold which allows for filtration, diffusion, absorption, excretion, or other biological function.

In some embodiments, the thin film membrane component can be manufactured using techniques such as spraying, electrospinning, thin film deposition, or other techniques know to the art in order to create a film of biologic material on a substrate or surface. In some embodiments, the thin film which comprises the basement membrane in the scaffold is constructed as a separate component and removed from the substrate, after which the membrane can then be further manipulated and subsequently incorporated into the scaffold along with the compartment, channel, or channel network component(s). In some embodiments, the thin film membrane is constructed, deposited, or otherwise created in conjunction with the channel network component. In some embodiments, the thin film membrane is deposited on a fugitive material of a specific architecture, which may optionally be further embedded or otherwise incorporated into a scaffold. In some embodiments, the fugitive material is evacuated from the scaffold during or after construction producing a thin film membrane component of a specific architecture related to the fugitive material. The thin film membrane, channel network(s), and other scaffold components may be manufactured without cells, cells may be seeded, encapsulated, or otherwise incorporated into the manufacture process of any or all of these components at any point during or after fabrication of the whole scaffold.

In some embodiments, the thin film membrane may be constructed from any biologic, synthetic, or composite material suitable for thin film deposition and capable of maintaining mechanical viability and barrier integrity between compartments within the scaffold as a whole. This thin film membrane may contain pores, slits, surface roughness, or other functional characteristics imparted during fabrication using techniques known to the art designed to improve function, biocompatibility, or other qualities of the membrane. This membrane may be of uniform or varying thicknesses in the range of 0.01 μm to 100 μm or greater.

The channel compartment(s) or network(s) contained within the scaffold and adjacent to the thin film membrane may be constructed using molds, filaments, extrusion, three-dimensional printing, or techniques using a variety of previously defined materials including fugitive materials to describe the lumen space, deposited in a given pattern or architecture. These material(s) may be arranged in hierarchical patterns or architecture so as to allow for branching flow patterns and high surface area. These channel networks may be patterned in a specific manner as to produce or promote function within the scaffold. These channel networks may be interconnected or separate.

The manufacture of the thin film membrane component may occur separately, in the presence of, or in conjunction with the manufacture of other scaffold components, such as the channel network(s). The manufacture of the thin film membrane may occur in a continuous manner during construction of the scaffold in conjunction with other manufacturing steps or processes. The membrane component(s) and channel network component(s) maybe be assembled sequentially or in a comprehensive manner so as to form a complete scaffold, and may be combined with other scaffold materials of similar or other composition during this process.

The thin film membrane component may be manufactured from biologic, synthetic, or composite materials such as collagen, gelatin, other hydrogels, cellulose, or other materials that can be deposited in a thin film and subsequently crosslinked, dried, gelled, cured, or otherwise stabilized to form a cohesive and mechanically stable thin film membrane. This thin film may undergo further treatment or manipulation to provide enhanced function or mechanics.

The channel network(s) components may constructed of material(s) that may or may not be fugitive in nature and can be dissolved, liquefied, or otherwise removed from the scaffold creating a negative lumen space comprising the channel compartment or network(s).

The bulk material within the scaffold not encompassed by the thin film membrane or channel network(s) components may be constructed from biologic, synthetic, or composite materials of similar or dissimilar composition as the membrane component, as long as it may be crosslinked to or otherwise bonded with the membrane in order to form a single cohesive scaffold.

This scaffold may be of appropriate composition as to be stabile mechanically, chemically, and otherwise under in-vitro and in-vivo conditions. This scaffold may be crosslinked or otherwise altered to maintain stability at temperatures appropriate for in-vitro cell culture and in-vivo implantation.

This scaffold may be constructed with cells or cells may be added after construction. The scaffold may support single or multiple cell types in any location within the scaffold, which may or may not enhance, promote, enable, or otherwise provide function(s) related to the cell or scaffold location. The membrane component(s), channel network component(s), and bulk scaffold component(s) may incorporate cells into their construction through encapsulation, engraftment, or other means known to the art. The thin film membrane and scaffold may be constructed of materials such that cellular remodeling, reconstruction, and maintenance of the scaffold occurs. The cell and scaffold interaction may improve or promote thin film membrane characteristics, qualities, or function.

The scaffold may be populated with cells that may provide cohesive, organized function such as diffusion, filtration, secretion, and absorption in conjunction with the thin film membrane(s), channel network(s), and bulk scaffold. In some embodiments, this function(s) may be performed in conjunction with or dependent on the contents of the channel networks and may make material, chemical, biological, or other alterations to the contents of the channel network(s).

In some embodiments of the invention, the scaffold and membrane are populated with cell types capable of providing hemodialysis functions potentially including but not limited to filtration, diffusion, absorption, and secretion of glucose, electrolytes, toxins, and other molecules. The scaffold and thin film membrane device may have channel network(s) perfused by blood in order to perform the previously mentioned functions on that blood. The scaffold may or may not have additional channel networks perfused by other fluids, such as dialysate, in order to facilitate or enhance this function. Embodiments of the invention may be used in an extracorporeal manner or may be implanted into a patient as an in vivo hemodialysis graft for therapeutic applications.

In some embodiments of the invention, the scaffold and membrane are populated with cell types capable of providing pulmonary functions potentially including but not limited to diffusion, gas exchange, absorption, and secretion. The scaffold and thin film membrane device may have channel network(s) perfused by blood in order to perform the previously mentioned functions on that blood. The scaffold may or may not have additional channel networks perfused by other fluids or gasses in order to facilitate or enhance this function. Embodiments of the invention may be used in an extracorporeal manner or may be implanted into a patient as an in vivo gas exchange device or lung tissue graft for therapeutic applications.

In some embodiments of the invention, the scaffold and membrane are populated with cell types capable of providing intestinal functions potentially including but not limited to absorption and secretion. The scaffold and thin film membrane device may have channel network(s) perfused by blood in order to perform the previously mentioned functions on that blood. The scaffold may or may not have additional channel networks perfused by other fluids or gasses in order to facilitate or enhance this function. Embodiment of the invention may be implanted into a patient to function as an in vivo gut tissue graft for therapeutic applications.

In some embodiments of the inventions disclosed herein, the sacrificial material can be shaped in the form of a branching channel network of increasing complexity and decreasing diameter. In some embodiments, the branches of a channel network subsequently merge to form a decreasing number of outflow branches of increasing diameter. In some embodiments, the branches of a channel network mimic natural perfusion patterns (e.g., exhibiting a large number of channels with a high surface area for diffusion within tissue constructs which can be perfused from a single source, allowing for functional channel architecture in conjunction with the thin film basement membrane). The methods disclosed herein enable multiple networks, channels, layers of networks, or other geometry and architecture that can be compounded in size and function to form tissue constructs of increasing size and sophistication.

In some embodiments of the inventions disclosed herein, channel diameter is determined by the dispensing method, material properties, and/or other parameters. Channel diameter can be any suitable diameter. In some embodiments, channel diameters (e.g., channel diameters in printed tissues or scaffolds) can include, but not be limited to, about 10 cm, 10 mm, 5 mm, 1 mm, 500 µm, 50 µm, 10 µm, 5 µm, 3 µm, 1 µm, 0.5 µm, 0.1 µm, 0.05 µm, 0.02 µm, or 0.01 µm. Significant advances in micro and nano-fabrication techniques, such as two photon polymerization printers can allow design and construction of sacrificial material components or hydrogel and polymer scaffolds with architecture at a resolution of 0.01-10 µm.

Some embodiments of the inventions disclosed herein include tissue or biological constructs consisting of a sacrificial material with thermally reversible gelation (such as Pluronic F127 gel (generic name poloxamer 407) and thin film basement membrane and scaffold components consisting of materials including, but not limited to, gelatin, collagen, chitosan, cellulose, PLA or other polymers or biologic materials or composite materials that can be assembled and crosslinked as described in previous examples.

Some embodiments of the inventions disclosed herein include fabrication of tissue or biological constructs consisting of a sacrificial material and basement membrane and scaffold components consisting of hydrogels such as gelatin, PLA, chitosan, composites of hydrogels or other hydrogel materials and composites of various concentrations and compositions. In some embodiments, varying the hydrogel materials and composites of various concentrations and compositions enable tuning of mechanical and biological properties which can enhance and further specialize tissue constructs for desired biological applications.

Some embodiments of the inventions disclosed herein include tissue or biological constructs, and methods of manufacturing therein, containing hydrogels, polymers, and compounds of materials which have been modified via techniques such as divalent metal ion removal, ligand attachment or other techniques known to the art in order to yield tunable mechanical and biological properties.

Some embodiments of the inventions disclosed herein include tissue or biological constructs, and methods of manufacturing therein, containing hydrogels, polymers, and compounds of materials which have been modified via addition of enhancing agents or compounds in order to yield tunable mechanical and biological properties. Examples of techniques include, but are not limited to, the addition of glycerin, sorbitol, propylene glycol, or other plasticizers into gelatin or gelatin composite hydrogels.

Some embodiments of the inventions disclosed herein include tissue or biological constructs, and methods of manufacturing therein, with the inclusion of additional material(s) such as polymer or hydrogel material providing a support matrix for the basement membrane material and construct. This additional material(s) such as polymer or hydrogel material may be constructed of similar material as the basement membrane or may be constructed of a complimentary hydrogel or polymer.

Some embodiments of the inventions disclosed herein include tissue or biological constructs, and methods of manufacturing therein, wherein the basement membrane component(s) and or scaffold component(s) are constructed of gelatin or other hydrogel or biocompatible material that has been altered to be photo curable using ultraviolet light of various wavelengths, such as gelatin methacrylate. Materials such as this, in varying concentrations can be created using published protocols or techniques know to the art.

Some embodiments of the inventions disclosed herein include tissue or biological constructs, and methods of manufacturing therein, wherein the basement membrane component(s) and or scaffold component(s) are applied in a multi-step process. This process may consist of application of a hydrogel or polymer material layer onto the sacrificial material, either before or after application of a curing solution or compound that acts to polymerize, gel, cure, or otherwise solidify the polymer or hydrogel material. In some embodiments, the application of gelatin and the subsequent application of a crosslinking solution (e.g., a solution comprising glutaraldehyde, transglutaminase, or other crosslinking enzymes or molecules) at, but not limited to, a concentration of about 0.01-5 g per 10 g gelatin.

Some embodiments of the inventions disclosed herein include tissue or biological constructs, and methods of manufacturing therein, wherein the curing solution for the basement membrane material is contained within the sacrificial material and the basement membrane material is cured, gelled, or otherwise solidified on contact with the sacrificial material. This method applies to basement membrane material that is atomized, sprayed, deposited, or otherwise applied to the sacrificial material, as well as to sacrificial material that is printed, extruded, or otherwise exposed to basement membrane material by submersion.

Some embodiments of the inventions disclosed herein include tissue or biological constructs, and methods of manufacturing therein, wherein any or all of the hydrogel or polymer materials used in construction of the tissue or construct may contain cells in suspension, adhered, or otherwise encapsulated so as to seed or deliver a cell source for the tissue construct.

Some embodiments of the inventions disclosed herein include tissue or biological constructs, and methods of manufacturing therein, containing hydrogels and polymers with the encapsulation or addition of biological factors to promote cell and tissue growth.

Some embodiments of the inventions disclosed herein include tissue or biological constructs, and methods of manufacturing therein, wherein the basement membrane is fabricated in conjunction with a substrate that imparts a pattern, porosity, or other physical condition on the membrane so as to improve function or biocompatibility or other qualities.

Some embodiments of the inventions disclosed herein include tissue or biological constructs, and methods of manufacturing therein, wherein the basement membrane is fabricated in conjunction with a substrate or material(s) that enhances the membrane through biologic or chemical means, such as addition of growth factors, ligands, encapsulated cells, or other biologically or biochemically relevant components.

Some embodiments of the inventions disclosed herein comprise scaffold or thin film membrane devices, and methods of manufacturing therein, having channel network(s) perfused by blood in order to perform functions related to that blood (e.g., filtration; diffusion; absorption; secretion of glucose, electrolytes, toxins, or other molecules; gas exchange; absorption; and secretion). In some embodiments, this scaffold or thin film membrane devices has additional channel networks perfused by other fluids or gases in order to facilitate or enhance functions related to that blood. In some embodiments, the scaffold or thin film membrane devices provides function in an extracorporeal or in-vivo manner to a patient for therapeutic applications.

Some embodiments of the inventions disclosed herein include scaffolds and membranes, and methods of manufacturing therein, that are populated with cell types capable of providing hemodialysis functions (e.g., filtration, diffusion, absorption, and/or secretion of glucose, electrolytes, toxins, and other molecules). In some embodiments, the scaffold or membrane is used in an extracorporeal manner. In some embodiments, the scaffold or membrane is implanted into a patient as an in-vivo hemodialysis graft for therapeutic applications.

Some embodiments of the inventions disclosed herein include scaffolds and membranes, and methods of manufacturing therein, that are populated with cell types capable of providing pulmonary functions (e.g., diffusion, gas exchange, absorption, and/or secretion). In some embodiments, the scaffold or membrane is used in an extracorporeal manner. In some embodiments, the scaffold or membrane is implanted into a patient as an in-vivo gas exchange device or lung tissue graft for therapeutic applications.

Some embodiments of the inventions disclosed herein include scaffolds and membranes, and methods of manufacturing therein, that are populated with cell types capable of providing intestinal functions (e.g., absorption and/or secretion). In some embodiments, the scaffold or membrane is used in an extracorporeal manner. In some embodiments, the scaffold or membrane is implanted into a patient to function as an in-vivo gut tissue graft for therapeutic applications.

One skilled in the art readily appreciates that the present invention is well adapted to carry out the objects and obtain the ends and advantages mentioned, as well as those inherent therein. The details of the description and the examples herein are representative of certain embodiments, are exemplary, and are not intended as limitations on the scope of the invention. Modifications therein and other uses will occur to those skilled in the art. These modifications are encompassed within the spirit of the invention. It will be readily apparent to a person skilled in the art that varying substitutions and modifications may be made to the invention disclosed herein without departing from the scope and spirit of the invention.

The articles "a" and "an" as used herein in the specification and in the claims, unless clearly indicated to the contrary, should be understood to include the plural referents. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all of the group members are present in, employed in, or otherwise relevant to a given product or process. Furthermore, it is to be understood that the invention provides all variations, combinations, and permutations in which one or more limitations, elements, clauses, descriptive terms, etc., from one or more of the listed claims is introduced into another claim dependent on the same base claim (or, as relevant, any other claim) unless otherwise indicated or unless it would be evident to one of ordinary skill in the art that a contradiction or inconsistency would arise. It is contemplated that all embodiments described herein are applicable to all different aspects of the invention where appropriate. It is also contemplated that any of the embodiments or aspects can be freely combined with one or more other such embodiments or aspects whenever appropriate. Where elements are presented as lists, e.g., in Markush group or similar format, it is to be understood that each subgroup of the elements is also disclosed, and any element(s) can be removed from the group. It should be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not in every case been specifically set forth in so many words herein. It should also be understood that any embodiment or aspect of the invention can be explicitly excluded from the claims, regardless of whether the specific exclusion is recited in the specification. For example, any one or more active agents, additives, ingredients, optional agents, types of organism, disorders, subjects, or combinations thereof, can be excluded.

Where the claims or description relate to a composition of matter, it is to be understood that methods of making or using the composition of matter according to any of the methods disclosed herein, and methods of using the composition of matter for any of the purposes disclosed herein are aspects of the invention, unless otherwise indicated or unless it would be evident to one of ordinary skill in the art that a contradiction or inconsistency would arise. Where the claims or description relate to a method, e.g., it is to be understood that methods of making compositions useful for performing the method, and products produced according to the method, are aspects of the invention, unless otherwise indicated or unless it would be evident to one of ordinary skill in the art that a contradiction or inconsistency would arise.

Where ranges are given herein, the invention includes embodiments in which the endpoints are included, embodiments in which both endpoints are excluded, and embodiments in which one endpoint is included and the other is excluded. It should be assumed that both endpoints are included unless indicated otherwise. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise. It is also understood that where a series of numerical values is stated herein, the invention includes embodiments that relate analogously to any intervening value or range defined by any two values in the series, and that the lowest value may be taken as a minimum and the greatest value may be taken as a maximum. Numerical values, as used herein, include values expressed as percentages. For any embodiment of the invention in which a numerical value is prefaced by "about" or "approximately", the invention includes an embodiment in which the exact value is recited. For any embodiment of the invention in which a numerical value is not prefaced by "about" or "approximately", the invention includes an embodiment in which the value is prefaced by "about" or "approximately".

As used herein "A and/or B", where A and B are different claim terms, generally means at least one of A, B, or both A and B. For example, one sequence which is complementary to and/or hybridizes to another sequence includes (i) one sequence which is complementary to the other sequence even though the one sequence may not necessarily hybridize to the other sequence under all conditions, (ii) one sequence which hybridizes to the other sequence even if the one sequence is not perfectly complementary to the other sequence, and (iii) sequences which are both complementary to and hybridize to the other sequence.

"Approximately" or "about" generally includes numbers that fall within a range of 1% or in some embodiments within a range of 5% of a number or in some embodiments within a range of 10% of a number in either direction (greater than or less than the number) unless otherwise stated or otherwise evident from the context (except where such number would impermissibly exceed 100% of a possible value). It should be understood that, unless clearly indicated to the contrary, in any methods claimed herein that include more than one act, the order of the acts of the method is not necessarily limited to the order in which the acts of the method are recited, but the invention includes embodiments in which the order is so limited. It should also be understood that unless otherwise indicated or evident from the context, any product or composition described herein may be considered "isolated".

As used herein the term "comprising" or "comprises" is used in reference to compositions, methods, and respective component(s) thereof, that are essential to the invention, yet open to the inclusion of unspecified elements, whether essential or not.

As used herein the term "consisting essentially of" refers to those elements required for a given embodiment. The term permits the presence of additional elements that do not materially affect the basic and novel or functional characteristic(s) of that embodiment of the invention.

The term "consisting of" refers to compositions, methods, and respective components thereof as described herein, which are exclusive of any element not recited in that description of the embodiment.

EXAMPLES

Example 1

In one example of this invention, a thin film basement membrane scaffold is assembled as follows:

In step 1, a thin film of a biocompatible basement membrane material or a combination of such basement membrane materials is deposited on a substrate using techniques known to the art such as thin film deposition using physical or chemical methods. This membrane is then cured, dried, partially or fully crosslinked, or otherwise solidified and removed from the substrate to form a uniform thin film membrane component.

In step 2, a blueprint of one or more channel networks constructed of one or multiple sacrificial materials and deposited onto the surface(s) of the thin film membrane component, forming a component containing thin film membrane and channel network(s). This can be accomplished using techniques know in the art including but not limited to extrusion, molding, milling, or additive printing. If necessary, a mechanical support material can be used, which may or may not also be a sacrificial material.

In step 3, one or multiple thin film membrane and channel components can be embedded in either a sacrificial material or a permanent matrix material that may be permanently crosslinked to the thin film membrane component. The material may or may not contain cells and may be used to modify mechanical properties of the construct such as elasticity, tensile strength, and color. The material may also provide additional mechanical or biological function to support or enhance the function of the initial construct.

In step 4, the sacrificial channel material(s) is (are) removed, leaving one or multiple channel networks and/or spaces lined by a thin film membrane with or without support structure behind.

In step 5, the channel network(s), compartment, and/or lumen spaces can be repopulated with one or multiple epithelial and or endothelial cell types.

Example 2

In another example of this invention, a thin film basement membrane scaffold is assembled as follows:

In step 1, a component containing one or more channel networks is generated from one or multiple sacrificial materials. This can be accomplished using techniques know in the art including but not limited to extrusion, molding, milling, or additive printing. If necessary, a mechanical support material or scaffold material can be used, which may or may not also be a sacrificial material.

In step 2, this component is then partially or fully coated with a thin film of a biocompatible basement membrane material or a combination of such basement membrane materials using techniques known to the art such as thin film deposition using physical or chemical methods.

Step 1 and 2 can be accomplished in a layering technique (alternating deposition of sacrificial material followed by thin film followed by sacrificial material, etc.) or in a sequential fashion (sacrificial material or materials followed by thin film deposition).

In step 3 the resulting construct can be embedded in either a sacrificial material or a permanent matrix material that may be permanently crosslinked to the membrane component. The resulting construct may incorporate one or multiple thin film membrane and channel constructs. The permanent material may or may not contain cells and may be used to modify mechanical properties of the construct such as elasticity, tensile strength, and color. The material may also provide additional mechanical or biological function to support or enhance the function of the initial construct.

In step 4, the sacrificial material(s) is (are) removed, leaving one or multiple channel networks and/or spaces lined by a thin basement membrane with or without support structure behind.

In step 5, the channel network(s) and/or lumen spaces can be repopulated with one or multiple epithelial and or endothelial cell types.

What is claimed is:

1. A composition comprising a thin film having a thickness of about 10 μm or less, wherein
    the thin film comprises functional basement membrane material, wherein the functional basement membrane material comprises decellularized tissue that has been homogenized or liquified;
    the thin film defines a boundary between a first interior volume and a second interior volume, wherein at least one of the first interior volume and second interior volume forms a vascular channel network with a volume of about 0.01 mL to about 10 L; and
    the thin film is capable of fluid filtration, gas diffusion, secretion or absorption of an electrolyte, diffusion of a hormone, or combinations thereof.

2. The composition of claim 1, wherein the thin film has a thickness of about 1 μm or less.

3. The composition of claim 1, wherein the vascular channel network has a volume of about 1 mL to about 10 L.

4. The composition of claim 1, further comprising a cellular scaffold.

5. The composition of claim 1, comprising multiple films defining multiple interior volumes in a three-dimensional space.

6. The composition of claim 1, wherein the first interior volume and the second interior volume are each connected to an exterior space.

7. The composition of claim 1, wherein at least one of the first interior volume and second interior volume comprise cells of one or more cell types.

8. The composition of claim 7, wherein the cells comprise cells adhered to a surface of the thin film.

9. The composition of claim 7, wherein the cells comprise epithelial cells.

10. The composition of claim 1, wherein the first interior volume comprises a first vascular network comprising human vascular endothelial cells and the second interior volume comprises a second vascular network comprising human renal epithelial cells, wherein the composition, when connected to a blood circulation system of a patient, is capable of hemodialysis.

11. The composition of claim 1, wherein the first interior volume comprises a first vascular network comprising human vascular endothelial cells and the second interior volume comprises a second vascular network comprising human pulmonary epithelial cells, wherein the composition, when connected to a blood circulation system of a patient, is capable of gas exchange.

12. The composition of claim 1, wherein the first interior volume comprises a first vascular network comprising human vascular endothelial cells and the second interior volume comprises one or more luminal spaces comprising human intestinal epithelial cells, wherein the composition further comprises interstitial cells and muscle cells outside of the first and second interior volumes, wherein the composition is capable of peristalsis and, when connected to a blood circulation system of a patient, is capable of nutrient absorption into the blood of the patient.

13. The composition of claim 1, wherein the first interior volume comprises a first vascular network comprising human vascular endothelial cells and the second interior volume comprises a second vascular network comprising human endocrine cells, wherein the composition, when connected to a blood circulation system of a patient, is capable of diffusing hormones or other substances into the blood of the patient.

14. A method of making a composition, comprising:
 a. generating a first sacrificial structure comprising one or more sacrificial materials on a support structure;
 b. applying a thin film layer comprising functional basement membrane material to the first sacrificial structure, wherein the thin film layer has a thickness of about 10 μm or less and wherein the first sacrificial structure contacts a first side of the thin film layer;
 c. applying a sacrificial material to a second side of the thin film layer to form a second sacrificial structure and embedding the second sacrificial structure in a material;
 d. removing the sacrificial material to provide a first interior volume and a second interior volume having a boundary defined by the thin film layer, thereby making the composition,
 wherein at least one of the first interior volume and second interior volume forms a vascular channel network with a volume of about 0.01 mL to about 10 L, wherein the functional basement membrane material comprises decellularized tissue that has been liquefied or homogenized.

15. The method of claim 14, wherein the support structure comprises a cellular scaffold.

16. The method of claim 14, wherein the first interior volume and the second interior volume are each connected to an exterior space.

17. The method of claim 14, further comprising a step (e) of populating at least one of the first interior volume and second interior volume with cells of one or more cell types.

18. The method of claim 17, wherein the cells comprise epithelial cells.

19. The method of claim 17, wherein the cells comprise endothelial cells.

* * * * *